US006632895B1

(12) United States Patent
Melchiors et al.

(10) Patent No.: US 6,632,895 B1
(45) Date of Patent: Oct. 14, 2003

(54) FUNCTIONALIZED ALKOXYAMINE INITIATORS

(75) Inventors: Martin Melchiors, Leverkusen (DE); Hartwig Höcker, Aachen (DE); Helmut Keul, Aachen (DE); Dirk Achten, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 453 days.

(21) Appl. No.: 09/652,203

(22) Filed: Aug. 31, 2000

(30) Foreign Application Priority Data

Sep. 7, 1999 (DE) ........................................ 199 42 614
Sep. 7, 1999 (DE) ........................................ 199 42 615

(51) Int. Cl.[7] .................................................. C08F 4/42

(52) U.S. Cl. ......................... 526/90; 526/205; 526/217; 526/220; 526/318; 526/319; 526/341; 564/1; 564/300; 564/301

(58) Field of Search ......................... 526/90, 205, 217, 526/220, 318, 319, 341; 564/1, 300, 301

(56) References Cited

U.S. PATENT DOCUMENTS

| | | | |
|---|---|---|---|
| 4,581,429 A | 4/1986 | Solomon et al. | 526/220 |
| 5,322,916 A | 6/1994 | O'Brien et al. | 528/183 |
| 5,401,804 A | 3/1995 | Georges et al. | 525/267 |
| 5,412,047 A | 5/1995 | Georges et al. | 526/204 |
| 5,449,724 A | 9/1995 | Moffat et al. | 526/204 |
| 5,549,998 A | 8/1996 | Georges et al. | 430/109 |

FOREIGN PATENT DOCUMENTS

| | | |
|---|---|---|
| EP | 911 350 | 4/1999 |
| WO | 95/26987 | 10/1995 |
| WO | 97/46593 | 12/1997 |

OTHER PUBLICATIONS

Hawker et al. "Initiating Systems for Nitroxide–Mediated "Living" Free Radical Polymerizations: Synthesis and Evaluation", vol. 26, No. 16, Jul. 29, 1996 (p. 5245–5254).*

Macromolecules, (month unavailable), 1998, 31, pp. 5955–5957, Krzysztof Matyjaszewski et al "Simple and Efficient Synthesis of Various Alkoxyamines for Stable Free Radical Polymerization".

Macromolecules, (month unavailable), 1998, 31, pp. 6380–6382, David E. Bergbreiter et al.

"Meisenheimer Rearrangement of Allyl N–Oxides as a Route to Initiators for Nitroxide–Medicated"Living" Free Radical Polymerizations".

Macromolecules, (month unavailable), 1998, 31, pp. 4659–4661, Yozo Miura et al, "High–Yield Synthesis of Alkoxyamine Initiators Carrying a Functional Group by Reaction of Ethylbenzenes with Di–tert–butyl Diperoxalate in the Presence of Nitroxides".

Macromolecules, (month unavailable), 1997, 30, pp. 6445–6450, Rebecca Braslau, et al "Low–Temperature Preparations of Unimolecular Nitroxide Initiators for"Living" Free Radical Polymerizations".

Makromol. Chem. Rapid Commun. (month unavailable), 1982, pp. 127–132, Takayuki Otsu et al, "Role of Initiator–Transfer Agent–Terminator (Iniferter) in Radical Polymerizations: Polymer Design by Organic Disulfides as Iniferters".

J. Am. Chem. Soc., Jul. 8, 1994, 116, pp. 11185–11186, Craig J. Hawker, "Molecular Weight Control by a "Living" Free–Radical Polymerization Process".

Macromolecules, (month unavailable), 1995, 28, pp. 2993–2995, Craig J. Hawker et al, "Accurate Control of Chain Ends by a Novel"Living" Free–Radical Polymerization Process".

J. Am. Chem. Soc., 1998, 120 (37), 9481–9495, XP002149956, Dennis J. Gravert, et al, "Soluble Supports Tailored for Organic Synthesis: Parallel Polymer Synthesis via Sequential Normal/Living Free Radical Processes".

J. Am. Chem. Soc., 1996, 118 (46), 11467–11471, XP000960412, Craig J. Hawker, et al, "Radical Crossover in Nitroxide Mediated"Living" Free Radical Polymerizations".

J. Org. Chem., 1998, 63 (21), 7130–7131, XP000960555, Ullrich Jahn, "Highly Efficient Generation of Radicals from Ester Enolates by the Ferrocenium Ion. Application to Selective.Alpha.–Oxygenation and Dimerization Reactions of Esters".

* cited by examiner

*Primary Examiner*—David W. Wu
*Assistant Examiner*—William Cheung
(74) *Attorney, Agent, or Firm*—Joseph C. Gil; Thomas W. Roy

(57) ABSTRACT

The invention relates to a new process for the preparation of functionalized alkoxyamine initiators, new alkoxyamine initiators based on (meth)acrylate which are prepared by this process, and their use for the preparation of polymers.

11 Claims, No Drawings

FUNCTIONALIZED ALKOXYAMINE INITIATORS

BACKGROUND OF THE INVENTION

1. Field of the invention

The present invention relates to a new process for the preparation of functionalized alkoxyamine initiators, new alkoxyamine initiators based on (meth)acrylate which are prepared by this process, and their use for the preparation of polymers.

2. Description of the Prior Art

Living free radical polymerization is a relatively young method of controlled free radical polymerization. It combines the advantages of a conventional free radical polymerization (simple synthesis process, broad monomer base) with those of a living polymerization (polymers of defined structure, molecular weight and distribution and end group functionality). The aim of precise control of free radical polymerization is achieved here by a reversible chain termination or blocking ("end-capping") after each growth step. The equilibrium concentration of the polymerization-active ("living") chain ends in this case is so low compared with the equilibrium concentration of the blocked ("dormant") chain ends that termination and transfer reactions are severely suppressed compared with the growth reaction. Since the end-capping proceeds reversibly, all the chain ends remain "living" if no termination reagent is present. This allows control of the molecular weight, a low polydispersity and controlled functionalization of the chain ends by termination reagents.

Controlled free radical polymerization using tetraalkythiuram disulfides is described by Otsu et al. (Makromol. Chem., *Rapid Commun*. 1982, 3, 127–132).

U.S. Pat. No. 4,581,429 discloses alkoxyamines which are formed by reaction of linear or cyclic nitroxides, such as 2,2,6,6-tetra-methylpiperidin-1-oxyl (TEMPO) with organic carbon-based free radicals, and a process for the preparation of vinyl polymers using these compounds as initiators. At temperatures >100° C., the C—ON bond can be cleaved reversibly to re-form the C radical ("active species") and the stable nitroxide radical. The equilibrium lies far on the side of the alkoxyamine ("dormant species").

The result of this reaction is a low, stationary, concentration of free radicals which, in the free radical polymerization of vinyl monomers, means that bimolecular termination reactions are disadvantaged kinetically compared with the unimolecular growth reaction. Side reactions are thus largely suppressed and a "living" reaction procedure is possible for the free-radical polymerization. The use of alkoxyamine initiators which additionally carry functional groups is not described.

The preparation of vinyl polymers by living free radical polymerization ("Stable Free Radical Polymerization", SFRP) on the basis of alkoxyamines is described by Hawker et al. (*J. Am. chem. Soc*. 1994, 116, 11185*; Macromolecules* 1995, 28, 1993) and Georges et al. (Xerox Comp., U.S. Pat. No. 5,322,912, U.S. Pat. No. 5,401,804, U.S. Pat. No. 5,412,047, U.S. Pat. No. 5,449,724, WO 94/11412, WO 95/26987 and WO 95/31484). The carbon radicals are prepared by addition of free radical initiators (peroxides or azo initiators) on to monomers which can be polymerized by free radicals; these free radicals are then captured in situ by TEMPO to give alkoxyamines. These alkoxyamines are the actual initiators, since they are cleaved reversibly at temperatures >100° C. into free radicals and can thus initiate polymerization of the monomers metered in. The use of functionalized alkoxyamine initiators would thus allow the synthesis of polymers of controlled end group functionality in a simple manner if the functional groups of the alkoxyamine initiators remain in the terminal position in the polymer.

Various working groups have concerned themselves with the synthesis of alkoxyamine initiators, and specifically those functional alkoxyamine initiators for SFRP of vinyl monomers. The following partly functionalized alkoxyamine initiators I–IV have been prepared by this synthesis by reaction of a free radical species with a stable nitroxide radical, by nucleophilic substitution reactions or oxidative addition.

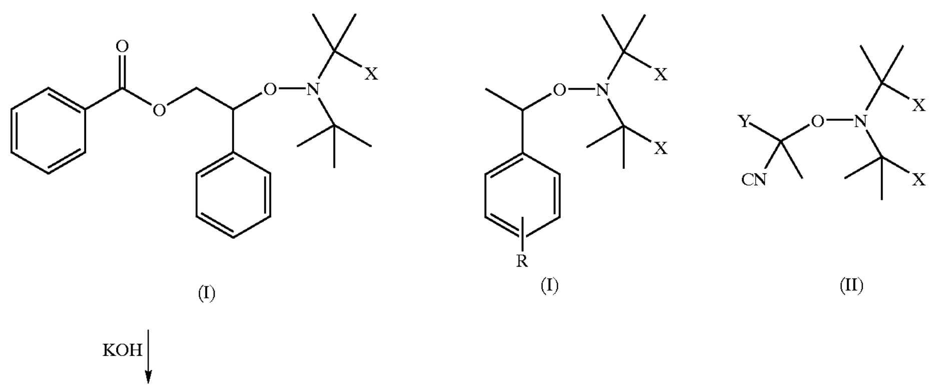

-continued

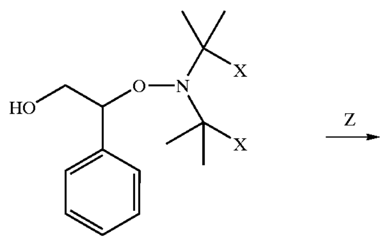

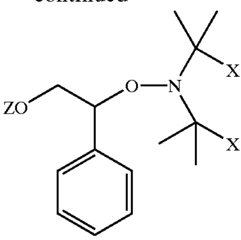

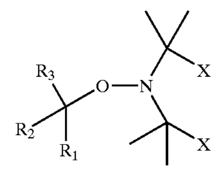

(I)

R = Br, COOEt, OMe, $CH_2OH$, Li, CHO
$R_1$,$R_2$,$R_3$ = various radicals, ester, alkyl, acyl
X = aryl, alkyl (cyclic or open-chain, functionalized)
Y = various radicals, alkyl, substituted alkyls, aryls
Z = a reagent which reacts with HO— to give an ester or ether Hawker el al. (*Macromolecules* 1996, 29, 5245–5254) developed a synthesis route for species I in which dibenzoyl peroxide free radical initiator initially introduced into the reaction vessel is captured by a stable nitroxide radical after addition on to a styrene monomer. Subsequent hydrolysis of the ester function gives a mono- or difunctional alkoxyamine initiator, depending on the substitution of the nitroxide radical. This process shows a low selectivity and gives only yields of <<40% of functionalized products.

The synthesis of alkoxyamine initiators of type II by the method of Hawker et al. (*Macromolecules* 1996, 29, 5245–5254), Yozo Miura et al. (*Macromolecules* 1998, 31, 4659–4661) and Braslau et al. (*Macromolecules* 1997, 30, 6445–6450) takes place with free radical initiators which, after their dissociation, can abstract activated hydrogen atoms from suitable substrates. Typical initiators are di-tert-butyl peroxide, di-tert-butyl hyponitrite and di-tert-butyl diperoxalate. Yields of these reactions are in the range from 40 to 90%. By using substituted aromatics (Br, COOEt, OMe), the synthesis of hydroxy-functional alkoxyamine initiators is possible in further reaction steps (Yozo Miura et al. *Macromolecules* 1998, 31, 4659–4661). The expensive multi-stage reaction procedure via organometallic intermediate stages makes this process scarcely realizable industrially and economically uninteresting.

Compounds of type III were obtained by Hawker et al. (*Macromolecules* 1996, 29, 5245–5254) by capturing the carbon radicals formed on dissociation of azo free radical initiators. By using expensive functionalized azo free radical initiators, synthesis of functionalized alkoxyamine initiators is thus possible. The yields of this reaction are <30%.

Alkoxyamine initiators of type I and IV were prepared by Matyjaszewski et al. (*Macromolecules* 1998, 31, 5955–5957) by reaction of benzylic or otherwise activated bromine compounds with a system, similar to ATRP (Atom Transfer Radical Polymerisation), of $Cu^0/Cu^{2+}$ and a substituted bipyridine in the presence of a stable nitroxide radical. A carbon radical is generated here by an ATRA reaction (Atom Transfer Radical Addition) with abstraction of the bromine atom, and is captured immediately by the nitroxide radical. The yields for this reaction are between 76 and 92%; functionalized alkoxyamine initiators were not prepared.

Braslai el al. (*Macromolecules* 1997, 30, 6445–6450) report on the synthesis of alkoxyamine initiators of type II and IV by various demanding multi-stage nucleophilic and oxidative or photooxidative addition routes with yields of 30–78%. Functionalized alkoxyamine initiators were not prepared.

Another route to alkoxyamine initiators according to Bergbreiter et al. (*Macromolecules* 1998, 31, 6380–6382) leads to N-allyloxyamines in yields of 10 to 74% starting from allylic amines. Functional alkoxyamine initiators were not prepared.

With none of the methods described can functionalized alkoxyamines with 1 or 2 functional groups which are capable of a further reaction or crosslinking with the known functional groups in coatings chemistry be prepared in an industrially simple manner and in high yields.

The object of the present invention was therefore to provide a process for the preparation of functional initiators of the type In—OH and/or Y—In—OH which does not have the abovementioned disadvantages of the prior art, wherein "In" represents a substituted hydrocarbon radical which is capable of initiating an SFRP and Y represents a functional group which is capable of a further reaction or crosslinking with the known functional groups in coatings chemistry.

SUMMARY OF THE INVENTION

The present invention relates to a process for the preparation of alkoxyamine initiators of the formula (I)

(I)

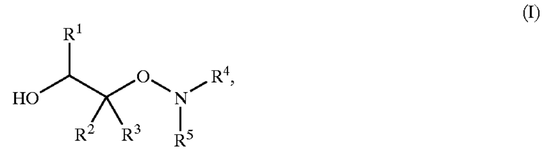

wherein $R^1$, $R^2$ and $R^3$ are the same or different and represent H, $C_1$–$C_{20}$-(cyclo)alkyl, $C_6$–$C_{24}$-aryl, halogen, CN, $C_1$–$C_{20}$-(cyclo)alkyl ester or -amide or $C_6$–$C_{24}$-aryl ester or -amide, and $R^4$ and $R^5$ are the same or different and represent aliphatic, cycloaliphatic or mixed aliphatic/aromatic radicals having 1 to 24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (i.e. not hydrogen) or a double-bonded carbon, oxygen, sulfur or nitrogen atom and a further organic substituent (not hydrogen), and wherein at least one of the radicals $R^4$ and $R^5$ can contain a functional group Y which is capable of a further reaction or crosslinking with the known functional groups in coatings chemistry, wherein A) a monomer which can be polymerized by free radicals, of the formula (M)

$HR^1C{=}CR^2R^3$, wherein $R^1$, $R^2$ and $R^3$ are the same or different and represent H, $C_1$–$C_{20}$-(cyclo)alkyl, $C_6$–$C_{24}$-aryl, halogen, CN, $C_1$–$C_{20}$-(cyclo)alkyl ester or -amide or $C_6$–$C_{24}$-aryl ester or -amide, is reacted in a solvent with B) a system, which produces free radicals, of B1) a compound having a reducing action, B2) a compound which can be split into one or more free radicals by the action of component B1, B3) a cyclic or acyclic nitroxide of the formula (N)

$R^4R^5NO$ wherein $R^4$ and $R^5$ are the same or different and represent aliphatic, cycloaliphatic or mixed aliphatic/aromatic, optionally substituted radicals having 1 to 24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (i.e. not hydrogen) or a double-bonded carbon, oxygen, sulfur or nitrogen atom and a further organic substituent (not hydrogen), and wherein at least one of the radicals $R^4$ and $R^5$ can contain a functional group Y which is capable of a further reaction or crosslinking with the known functional groups in coatings chemistry.

The process according to the invention allows simple, one-stage preparation of the functionalized alkoxyamine initiators in high yields starting from inexpensive, easily accessible base chemicals.

The present invention also relates to new alkoxyamine initiators prepared by the process according to the invention, of the formula (II)

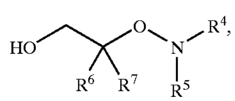

(II)

wherein $R^4$ and $R^5$ have the meaning given in the case of formula (I), $R^6$ can be H or a $C_1$–$C_{20}$-(cyclo)alkyl radical and $R^7$ can be a linear or branched $C_1$–$C_{24}$-(cyclo) alkyloxocarbonyl radical ((cyclo)aliphatic ester group) or CN.

The invention also relates to the use of the alkoxyamine initiators of the formulae (I) and (II) prepared by the process according to the invention, in particular of the new alkoxyamine initiators of the formula II, for the preparation of polymers.

DETAILED DESCRIPTION OF THE INVENTION

Monomers (M) of component (A) include all the olefins which can be polymerized by free radicals and are known from the prior art. These olefins can also be substituted. Possible substituents for the olefins include:

H linear or branched alkyl radicals having 1 to 20 carbon atoms, which can optionally also carry further substituents, α.β-unsaturated linear or branched alkenyl or alkinyl radicals, which can optionally also carry further substituents, cycloalkyl radicals, which can also carry heteroatoms, such as O, N, or S in the ring and optionally further substituents, optionally substituted aryl or heteroaryl radicals, halogen, CN, $CF_3$, COOR and COR.

The double bond of the monomers (M) can also be part of a ring, such as in the case of cyclic olefins or olefiically unsaturated cyclic anhydrides or imides.

Monomers which are preferably employed are (meth) acrylic acid esters of $C_1$–$C_{20}$-alcohols, acrylonitrile, cyanoacrylic acid esters of $C_1$–$C_{20}$-alcohols, maleic acid di-esters of $C_1$–$C_6$-alcohols, maleic anhydride, vinylpyridines, vinyl(alkylpyrroles), vinyloxazoles, vinyloxazolines, vinylthiazoles, vinylimidazoles, vinylpyrimidines, vinyl ketones, styrene or styrene derivatives which carry a $C_1$–$C_6$-alkyl radical or halogen in the α-position and carry up to 3 further substituents on the aromatic ring.

Methyl acrylate, methyl methacrylate, butyl acrylate, butyl methacrylate, 2-ethyl-hexyl acrylate, cyclohexyl methacrylate, isobornyl methacrylate, maleic anhydride or styrene are particularly preferably employed.

B1 The compound having a reducing action is a reducing agent, such as transition metal compounds, sulfur compounds of a low oxidation level or compounds which can easily be enolized. Sodium hydrogen sulfite, carbonyl compounds which can easily be enolized, such as ascorbic acid and hydroxy-acetone, and metal ions, such as $Fe^{2+}$, $Ti^{3+}$ and $Cu^{1+}$, are preferably employed. $Fe^{2+}$, $Ti^{3+}$ and $Cu^{1+}$ in the form of inorganic salts or organic salts are particularly preferred.

B2 Component B2 is a compound which can be split into one or more free radicals by the action of component B1. Hydrogen peroxide is preferably employed as component B2 in the context of the present invention. The use of hydrogen peroxide as a supplier of free radicals is mentioned in none of the documents described above in the prior art for the synthesis of alkoxyamine initiators.

Hydrogen peroxide is a thermodynamically metastable compound as the pure substance and in aqueous solution (e.g. 30% perhydrol). The rate of dissociation of hydrogen peroxide is greatly increased, even at room temperature, by catalysts, (e.g. finely divided metals, manganese dioxide, dust particles, non-metal ions, such as $I^-$, $IO_3^-$ and $OH^-$, or metal ions, such as $Fe^{2+}$, $Fe^{3+}$ and $Cu^{2+}$). Hydroxyl radicals can be generated in a controlled manner from hydrogen peroxide by thermal decomposition of the hydrogen peroxide or by one-electron redox reactions of the hydrogen peroxide with a suitable electron donor. Typical compounds are e.g. sodium hydrogen sulfite, carbonyl compounds which can easily be enolized, such as ascorbic acid and hydroxyacetone, and metal ions, such as $Fe^{2+-}$, $Ti^{3+}$ and $Cu^{1+}$. The reaction of $Fe^{2+}$ with hydrogen peroxide to give HO. radicals which can be used for oxidation of organic compounds has become known by the name Fenton's reagent:

$$Fe^{2+}+HO—OH \rightarrow Fe^{3+}+HO.+HO^{-}.$$

The $HO^{-}$ formed in the redox reaction can also initiate the peroxide dissociation.

In the presence of saturated organic compounds HR, the hydroxy radical can react with abstraction of H. Furthermore, the HO. radicals are also capable of adding on to multiple bonds of unsaturated organic compounds.

In the process according to the invention for the preparation of an alkoxyamine initiator of the formula (I), an OH radical adds on to a C═C double bond of the monomer (M) which can be polymerized by free radicals, and thus introduces a hydroxyl group into the alkoxyamine initiator.

In principle, other compounds of the type R'—O—O—R" which form free radicals can also be used as component B2 if the radicals R' and R" contain a functional group Y which is capable of a further reaction or crosslinking with the known functional groups in coatings chemistry, e.g. OH, $NH_2$, NHR or epoxide. However, the use of compounds of such a type as component B2 is not preferred.

B3 Component B3 comprises compounds which act as agents which trap free radicals and which capture the monomer radical formed from components A and (B1+B2) before a further reaction in the sense of a polymerization. In the present invention, cyclic or acyclic nitroxides of the formula (N) are employed as component B3. In formula (N), $R^4$ and $R^5$ are the same or different and denote aliphatic, cycloaliphatic or mixed aliphatic/aromatic radicals having 1 to 24 carbon atoms. The carbon atom of the radicals $R^4$ and $R^5$ directly adjacent to the alkoxyamine nitrogen atom is in each case substituted by 3 further organic substituents (i.e. not hydrogen) or a double-bonded carbon, oxygen, sulfur or nitrogen atom and a further organic substituent (not hydrogen), wherein at least one of the radicals $R^4$ and $R^5$ can contain a functional group Y which is capable of a further reaction or crosslinking with the known functional groups in coatings chemistry. $R^4$ and $R^5$ can also be part of a 4- to 8-membered ring.

Nitroxides of one of the following formulae (III) to (VI) are employed according to the invention as component B3

(III)

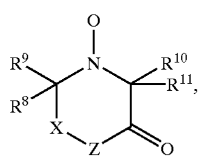

(IV)

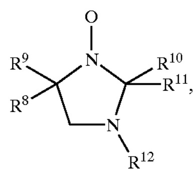

-continued (V)

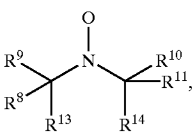

(VI)

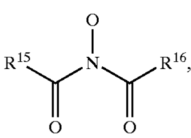

wherein in $R^8$, $R^9$, $R^{10}$ and $R^{11}$ are the same or different and represent $C_1$–$C_{20}$-(cyclo)alkyl or $C_6$–$C_{24}$-aryl radicals or $C_7$–$C_{24}$-aliphatic/aromatic hydrocarbon radicals, which can additionally contain cyano groups, ether groups, amide groups or OH groups and can also be part of a ring structure, wherein X can also be $CH_2$ or C═O, Z represents O or N—$R^{12}$ and $R^{12}$, $R^{15}$ and $R^{16}$ are the same or different and represent H or a $C_1$–$C_{20}$-(cyclo)alkyl or $C_6$–$C_{24}$-aryl radical or a $C_7$–$C_{24}$-aliphatic/aromatic hydrocarbon radical, wherein these substituents can also be part of a ring structure, and $R^{13}$ and $R^{14}$ are the same or different and denote $C_1$–$C_{20}$-(cyclo)alkyl, $C_6$–$C_{24}$-aryl or $C_7$–$C_{24}$-aliphatic/aromatic hydrocarbon radicals and can also be part of a ring structure, wherein $R^{13}$ and/or $R^{14}$ may contain functional groups chosen from substituted or unsubstituted phenyl, cyano, ether, hydroxyl, nitro, dialkyloxyphosphonyl or carbonyl-carrying groups and the groups $CR^8R^9R^{13}$ and/or $CR^{10}R^{11}R^{14}$ can also be part of an aromatic ring system or can form a phenyl group.

Components which are preferably used as component B3 are those of the formula (VII)

(VII)

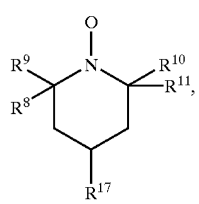

wherein $R^{17}$ is either hydrogen or a functional group Y which is capable of a further reaction or crosslinking with the known functional groups in coatings chemistry; Y,can be e.g. a hydroxyl group, amino group or epoxide group.

Nitroxides of formula VII where $R^8$═$R^9$═$R^{10}$═$R^{11}$═$CH_3$ and $R^{17}$═H, OH or $NH_2$ are particularly preferably employed as component B3.

In one possible way for carrying out the process according to the invention a solution of components A, B1 and B3 in a solvent or solvent mixture is initially introduced into the reaction vessel and the component B2 which forms free radicals is slowly metered in, with stirring. B2 is preferably metered in here as an aqueous solution in a 0.1- to 20-fold molar excess with respect to B3. B1 is employed in an equimolar amount, but preferably in an up to 20% molar excess, with respect to B3. The monomer A is employed in a 0.2- to 20-fold molar excess with respect to B3. Excess portions of the components, employed are removed again by distillation or extraction when the reaction has ended. The reaction takes place at temperatures between 0° C. and 150° C., preferably 40° C. to 100° C. It can be carried out in air or in an inert gas atmosphere; an inert gas atmosphere (e.g. nitrogen or argon) is preferably used. The pH of the reaction solution can optionally be adjusted to a range from 5 to 7 with substances such as $NaHCO_3$. With certain functional groups (e.g. $Y{=}NH_2$), it may be advantageous to provide the functional groups with a protective group during the reaction described (e.g. protection of amino groups as acetamides; later liberation of the amino function by hydrolysis with a base); for Y=OH, however, it is not necessary to use protective groups.

Solvents include water, alcohols, preferably methanol, ethanol or isopropanol, ethers, preferably diethyl ether, oligoethylene glycols or THF, carbonyl compounds, preferably acetaldehyde, acetone or methyl ethyl ketone, or any desired mixtures of the solvents mentioned.

The functionalized alkoxyamine initiators prepared according to the invention have the formula (I)

(I)

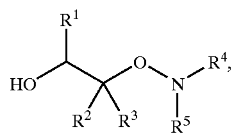

wherein in particular, new alkoxyamine initiators of the formula (II)

(II)

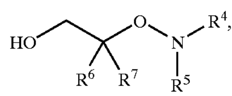

in which can be prepared in a simple manner and a high yield by the process according to the invention on the basis of acrylate and methacrylate monomers such as are conventionally employed in polyacrylate (co)polymers in lacquer technology. These new alkoxyamine initiators of the formula (II) contain at least one OH group; preferably, in at least one of the radicals $R^4$ and $R^5$ they also contain a further functional group Y which is capable of a further reaction or crosslinking with the known functional groups in coatings chemistry.

Particularly preferred new alkoxyamine initiators are those of the formula (IIb)

(IIb)

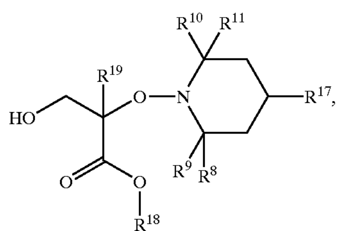

wherein $R^8$, $R^9$, $R^{10}$ and $R^{11}$ have the meaning given in the case of formula (VII), $R^{17}$ represents hydrogen or a functional group Y which is capable of a further reaction or crosslinking with the known functional groups in coatings chemistry and $R^{18}$ represents a (cyclo)aliphatic alkyl group having 1 to 20 carbon atoms and $R^{19}$ represents H or $CH_3$.

$R^{19}$ represents H or $CH_3$.

In particular, in formula (IIb) $R^8{=}R^9{=}R^{10}{=}R^{11}{=}CH_3$ and Y is one of the functional groups OH, $NH_2$ or NHR which are introduced into the alkoxyamine initiator via the nitroxide component B3.

The alkoxyamine initiators of the formula (I) prepared according to the invention can be used e.g. as free radical initiators for the preparation of vinyl (co)polymers or oligomers, in particular of those with functional groups as end groups.

EXAMPLES

Preparation according to the invention of the functionalized alkoxyamine initiators: All data in % are based on the weight.

Example 1

HOST: 1-Phenyl-1-(2',2',6',6'-tetramethyl-1'-piperidinyloxy)-2-hydroxyethane 0.12 mol $Fe(II)SO_4 \cdot 7H_2O$ (33.36 g) and 18.5 g $NaHCO_3$ (0.24 mol) were added to a homogeneous solution of 1 mol styrene (104.14 g) and 0.1 mol TEMPO (2,2,6,6-tetramethylpiperidin-1-oxyl, 15.6 g) in 300 ml methanol in a 1 l two-necked flask under a nitrogen atmosphere and the mixture was heated to 40° C. with vigorous stirring. 50 ml 30% $H_2O_2$ solution in 50 ml methanol were slowly added dropwise to the red reaction solution in the course of 5 h.

After the red coloration had disappeared—indication of a complete conversion of TEMPO—the Fe(III) hydroxide formed and unreacted $Fe(II)SO_4 \cdot 7H_2O$ and $NaHCO_3$ were removed from the reaction mixture by filtration. The filtrate was freed from methanol on a rotary evaporator at RT. The product (HOST) and styrene were separated from the aqueous phase by extraction with ether. The ethereal solution was dried over $Na_2SO_4$. The desiccant was filtered off and ether and styrene were stripped off on a rotary evaporator at 40° C. The monofunctionalized alkoxyamine initiator was obtained in a yield of 71%.

Example 2

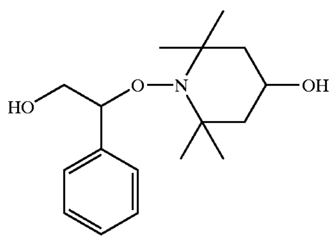

HOSTOH: 1-Phenyl-1-(4'-hydroxy-2',2',6',6'-tetramethyl-1'-piperidinyloxy)-2-hydroxyethane 0.12 mol Fe(II)$SO_4$. $7H_2O$ (33.36 g) and 18.5 g $NaHCO_3$ (0.24 mol) were added to a homogeneous solution of 1 mol styrene (104.14 g) and 0.1 mol 4-HO-TEMPO (4-hydroxy-2,2,6,6-tetramethylpiperidin-1-oxyl, 17.33 g) in 300 ml methanol in a 1 l two-necked flask under a nitrogen atmosphere and the mixture was heated to 40° C. with vigorous stirring. 50 ml 30% $H_2O_2$ solution in 50 ml methanol were slowly added dropwise to the red reaction solution in the course of 5 h.

After the red coloration had disappeared—indication of a complete conversion of 4-HO-TEMPO—the Fe(III) hydroxide formed and unreacted Fe(II)$SO_4$. $7H_2O$ and $NaHCO_3$ were removed from the reaction mixture by filtration. The filtrate was freed from methanol on a rotary evaporator at RT. The product (HOSTOH) and styrene were separated from the aqueous phase by extraction with ether. The ethereal solution was dried over $Na_2SO_4$. The desiccant was filtered off and ether and styrene were stripped off on a rotary evaporator at 40° C. The difunctionalized alkoxyamine initiator is obtained in a yield of 95%.

Example 3

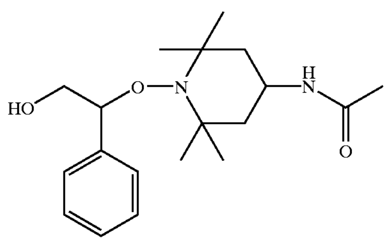

HOSTNHCOCH$_3$:1-Phenyl-1-(4'-acetylamido-2',2',6',6'-tetramethyl-1'-piperidinyloxy)-2-hydroxyethane 0.04 mol Fe(II)$SO_4$. $7H_2O$ (11.1 g) and 6.7 g $NaHCO_3$ (0.08 mol) were added to a homogeneous solution of 0.5 mol styrene (52.07 g) and 0.03 mol 4-acetylamido-TEMPO (4-acetylamido-2,2,6,6-tetramethylpiperidin-1-oxyl, 6.03 g) in 150 ml methanol in a 0.5 l two-necked flask under a nitrogen atmosphere and the mixture was heated to 40° C. with vigorous stirring. 20 ml 30% $H_2O_2$ solution in 20 ml methanol were slowly added dropwise to the red reaction solution in the course of 5 h.

After the red coloration had disappeared—indication of a complete conversion of 4-acetylamido-TEMPO—the Fe(III) hydroxide formed and unreacted Fe(II)$SO_4$. $7H_2O$ and $NaHCO_3$ were removed from the reaction mixture by filtration. The filtrate was freed from methanol on a rotary evaporator at RT. The product (HOSTNHCOCH$_3$) and styrene were separated from the aqueous phase by extraction with ether. The ethereal solution was dried over $Na_2SO_4$. The desiccant was filtered off and ether and styrene were stripped off on a rotary evaporator at 40° C. The monofunctionalized alkoxyamine initiator was obtained in a yield of 85%.

Example 4

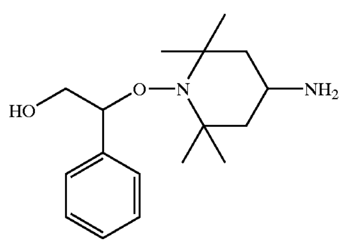

HOSTNH$_2$:1-Phenyl-1-(4'-amino-2',2',6',6'-tetramethyl-1'-piperidinyloxy)-2-hydroxy-ethane 0.0018 mol HOSTNHCOCH$_3$ (0.6 g) was added to a solution of 10 g KOH in 20 ml water and 20 ml ethylene glycol in a 200 ml Schlenk flask under a nitrogen atmosphere. The solution was heated at 100° C. for 12 h and thereafter extracted 5 times with 20 ml ether each time. The ethereal phase was washed twice with 30 ml of an aqueous HCl solution with a pH of 3. The product was now in the acid aqueous phase. 10 g KOH were added to this and it was extracted again with ether. The ethereal phase was dried over $Na_2SO_4$ and filtered, the ether was removed on a rotary evaporator and the product was dried under a high vacuum. The difunctionalized alkoxyamine initiator HOSTNH$_2$ was obtained as a white solid in a yield of 59%.

Example 5

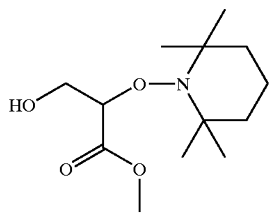

HOMAT: Methyl 3-Hydroxy-2-(2',2',6',6'-tetramethyl-1'-piperidinyloxy)-propionate 0.12 mol Fe(II)$SO_4$. $7H_2O$ (33.36 g) and 18.5 g $NaHCO_3$ (0.24 mol) were added to a homogeneous solution of 1 mol methyl acrylate (86.09 g) and 0.1 mol TEMPO (2,2,6,6-tetramethylpiperidin-1-oxyl, 15.6 g) in 300 ml methanol in a 1 l two-necked flask under a nitrogen atmosphere and the mixture was heated to 40° C. with vigorous stirring. 50 ml 30% $H_2O_2$ solution in 50 ml methanol were slowly added dropwise to the red reaction solution in the course of 5 h.

After the red coloration had disappeared—indication of a complete conversion of TEMPO—the Fe(III) hydroxide formed and unreacted $Fe(II)SO_4$. $7H_2O$ and $NaHCO_3$ were removed from the reaction mixture by filtration. The filtrate was freed from methanol on a rotary evaporator at RT. The product (HOMAT) and methyl acrylate were separated from the aqueous phase by extraction with ether. The ethereal solution was dried over $Na_2SO_4$. The desiccant was filtered off and ether and methyl acrylate were stripped off on a rotary evaporator at 40° C. The difunctionalized alkoxyamine initiator was obtained in a yield of 76%.

Example 6

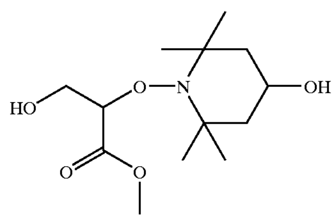

HOMATOH: Methyl 3-Hydroxy-2-(4'-hydroxy-2',2',6',6'-tetramethyl-1'-piperidinyloxy)-propionate 0.12 mol $Fe(II)SO_4$. $7H_2O$ (33.36g) and 18.5 g $NaHCO_3$ (0.12 mol) were added to a homogeneous solution of 1 mol methyl acrylate (86.09 g) and 0.1 mol 4-HO-TEMPO (4-hydroxy-2,2,6,6-tetramethylpiperidin-1-oxyl, 17.33 g) in 300 ml methanol in a 1 l two-necked flask under a nitrogen atmosphere and the mixture was heated to 40° C. with vigorous stirring. 50 ml 30% $H_2O_2$ solution in 50 ml methanol were slowly added dropwise to the red reaction solution in the course of 5 h.

After the red coloration had disappeared—indication of a complete conversion of 4-HO-TEMPO—the Fe(III) hydroxide formed and unreacted $Fe(II)SO_4$. $7H_2O$ and $NaHCO_3$ were removed from the reaction mixture by filtration. The filtrate was freed from methanol on a rotary evaporator at RT. The product (HOMATOH) and methyl acrylate were separated from the aqueous phase by extraction with ether. The ethereal solution was dried over $Na_2SO_4$. The desiccant was filtered off and ether and methyl acrylate were stripped off on a rotary evaporator at 40° C. The difunctionalized alkoxyamine initiator was obtained in a yield of 60%.

Example 7

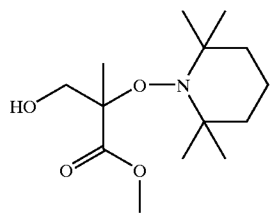

HOMMAT: Methyl 3-Hydroxy-2-methyl-2-(2',2',6',6'-tetramethyl-1'-piperidinyloxy)-propionate 0.06 mol $Fe(II)SO_4$. $7H_2O$ (16.68 g) and 9.25 g $NaHCO_3$ (0.12 mol) were added to a homogeneous solution of 0.5 mol methyl methacrylate (50 g) and 0.05 mol TEMPO (2,2,6,6-tetramethylpiperidin-1-oxyl, 7.8 g) in 150 ml methanol in a 0.5 l two-necked flask with a magnet core under a nitrogen atmosphere and the mixture was heated to 40° C. with vigorous stirring. 25 ml 30% $H_2O_2$ solution in 25 ml methanol were slowly added dropwise to the red reaction solution in the course of 5 h.

After the red coloration had disappeared—indication of a complete conversion of TEMPO—the Fe(III) hydroxide formed and unreacted $Fe(II)SO_4$. $7H_2O$ and $NaHCO_3$ were removed from the reaction mixture by filtration. The filtrate was freed from methanol on a rotary evaporator at RT. The product (HOMMAT) and methyl methacrylate were separated from the aqueous phase by extraction with ether. The ethereal solution was dried over $Na_2SO_4$. The desiccant was filtered off and ether and methyl methacrylate were stripped off on a rotary evaporator at 40° C. The monofunctionalized alkoxyamine initiator was obtained in a yield of 66%.

Example 8

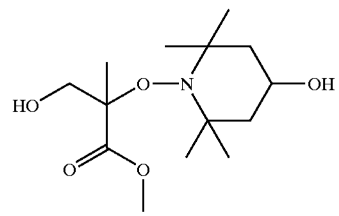

HOMMATOH: Methyl 3-Hydroxy-2-methyl-2-(4'-hydroxy-2',2',6',6'-tetramethyl-1'-piperidinyloxy)-propionate 0.06 mol $Fe(II)SO_4$. $7H_2O$ (16.68 g) and 9.25 g $NaHCO_3$ (0.12 mol) were added to a homogeneous solution of 0.5 mol methyl methacrylate (50 g) and 0.05 mol 4-HO-TEMPO (4-hydroxy-2,2,6,6-tetramethylpiperidin-1-oxyl, 8.66 g) in 150 ml methanol in a 0.5 l two-necked flask under a nitrogen atmosphere and the mixture was heated to 40° C. with vigorous stirring. 25 ml 30% $H_2O_2$ solution in 25 ml methanol were slowly added dropwise to the red reaction solution in the course of 5 h.

After the red coloration had disappeared—indication of a complete conversion of 4-HO-TEMPO—the Fe(III) hydroxide formed and unreacted $Fe(II)SO_4$. $7H_2O$ and $NaHCO_3$ were removed from the reaction mixture by filtration. The filtrate was freed from methanol on a rotary evaporator at RT. The product (HOMMATOH) and methyl methacrylate were separated from the aqueous phase by extraction with ether. The ethereal solution was dried over $Na_2SO_4$. The desiccant was filtered off and ether and methyl methacrylate were stripped off on a rotary evaporator at 40° C. After recrystallization from methylene chloride, the difunctionalized alkoxyamine initiator HOMMATOH was obtained as colourless crystals (yield: 37%).

The products of examples 1 to 8 can optionally be purified further by reprecipitation or recrystallization.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of mono- and difunctional alkoxyamine initiators of the formula (I)

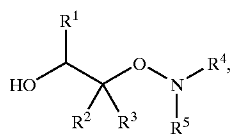

(I)

wherein $R^1$, $R^2$ and $R^3$ are the same or different and represent H, $C_1$–$C_{20}$-(cyclo)alkyl, $C_6$–$C_{24}$-aryl, halogen, CN, $C_1$–$C_{20}$-(cyclo)alkyl ester or -amide or $C_6$–$C_{24}$-aryl ester or -amide, and $R^4$ and $R^5$ are the same or different and represent aliphatic, cycloaliphatic or mixed aliphatic/aromatic radicals having 1 to 24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (i.e. not hydrogen) or a double-bonded carbon, oxygen, sulfur or nitrogen atom and a further organic substituent (not hydrogen), and wherein at least one of the radicals $R^4$ and $R^5$ can contain a functional group Y selected from the group consisting of hydroxy, primary amine, secondary amine and epoxide, wherein A) a monomer which can be polymerized by free radicals, of the formula (M)

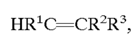

$HR^1C{=}CR^2R^3$, is reacted with

B) a system, which produces free radicals, of

B1) a compound having a reducing action,

B2) a compound which can be split into one or more free radicals by the action of component B1, B3) a cyclic or acyclic nitroxide of the formula (N)

$R^4R^5NO$ in a solvent.

2. The process of claim 1, wherein in formula (I) $R^1{=}H$, $R^2{=}H$ or a $C_1$–$C_{20}$-(cyclo)alkyl radical and $R^3$ is a linear or branched $C_1$–$C_{24}$-(cyclo)alkyloxocarbonyl radical or CN.

3. The process of claim 1, wherein component A is selected from the group consisting of methyl acrylate, methyl methacrylate, butyl acrylate, butyl methacrylate, 2-ethylhexyl acrylate, cyclohexyl methacrylate, isobornyl methacrylate, maleic anhydride and styrene.

4. The process of claim 1, wherein $Fe^{2+}$, $Ti^{3+}$ and $Cu^{1+}$ in the form of their inorganic or organic salts are used as component B1.

5. The process of claim 1, wherein component B2 is hydrogen peroxide.

6. The process of claim 1, wherein component B3, nitroxides of one of the following formulae (III) to (VI)

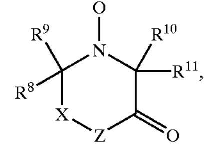

(III)

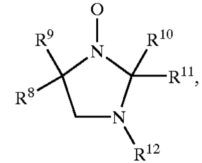

(IV)

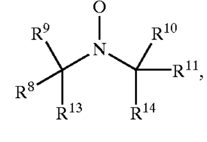

(V)

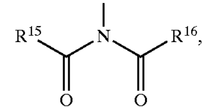

(VI)

are employed, wherein:

$R^8$, $R^9$, $R^{10}$ and $R^{11}$ are the same or different and represent $C_1$–$C_{20}$-(cyclo)alkyl or $C_6$–$C_{24}$-aryl radicals or $C_7$–$C_{24}$-aliphatic/aromatic hydrocarbon radicals, which can additionally contain cyano groups, ether groups, amide groups or OH groups and can also be part of a ring structure, wherein X can also be $CH_2$ or C=O, Z can represent O or N—$R^{12}$ and $R^{12}$, $R^{15}$ and $R^{16}$ are the same or different and represent H or a $C_1$–$C_{20}$-(cyclo)alkyl or $C_6$–$C_{24}$-aryl radical or a $C_7$–$C_{24}$-aliphatic/aromatic.

7. The process of claim 5, wherein as component B3, nitroxides of the formula (VII) are employed

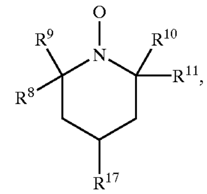

(VII)

wherein $R^8$, $R^9$, $R^{10}$ and $R^{11}$ are the same or different and represent $C_1$–$C_{20}$-(cyclo)alkyl or $C_6$–$C_{24}$-aryl radicals or $C_7$–$C_{24}$-aliphatic/aromatic hydrocarbon radicals, which can additionally contain cyano groups, ether groups, amide groups or OH groups and can also be part of a ring structure, $R^{17}$ represents hydrogen or a functional group Y.

8. The process of claim 7, wherein as component B3, nitroxides of the structural formula (VII) where $R^8{=}R^9{=}R^{10}{=}R^{11}{=}CH_3$ and $R^{17}{=}H$, OH or $NH_2$ are employed.

9. Alkoxyamine initiators of the formula (II)

(II)

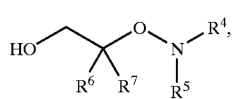

wherein $R^4$ and $R^5$ are the same or different and represent aliphatic, cycloaliphatic or mixed aliphatic/aromatic radicals having 1 to 24 carbon atoms, which can also be part of a 4- to 8-membered ring, wherein the carbon atom of the radicals $R^4$ and $R^5$ directly adjacent to the alkoxyamine nitrogen atom is in each case substituted by 3 further organic substituents (i.e. not hydrogen) or a double-bonded carbon, oxygen, sulfur or nitrogen atom and a further organic substituent (not hydrogen), and wherein at least one of the radicals $R^4$ and $R^5$ can contain a functional group Y selected from the group consisting of hydroxy, primary amine, secondary amine and epoxide, $R^6$ represents H or a $C_1$–$C_{20}$-(cyclo)alkyl radical and $R^7$ represents a linear or branched $C_1$–$C_{24}$-(cyclo) alkyloxocarbonyl radical (i.e. a (cyclo)aliphatic ester group) or CN.

10. Alkoxyamine initiators of the formula (IIb)

(IIb)

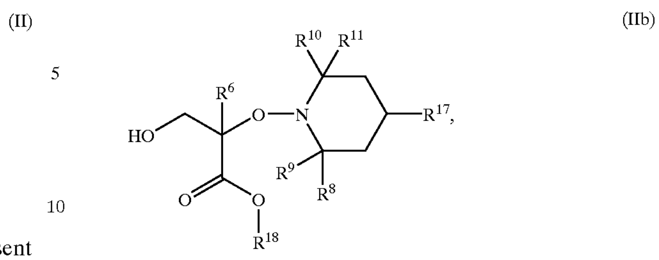

wherein $R^8$, $R^9$, $R^{10}$ and $R^{11}$ are the same or different and represent $C_1$–$C_{20}$-(cyclo)alkyl or $C_6$–$C_{24}$-aryl radicals or $C_7$–$C_{24}$-aliphatic/aromatic hydrocarbon radicals, which can additionally contain cyano groups, ether groups, amide groups or OH groups and can also be part of a ring structure, $R^{17}$ represents hydrogen or a group selected from the group consisting of hydroxy, primary, amine, secondary amine and epoxide $R^{18}$ is a (cyclo)aliphatic alkyl group having 1 to 20 carbon atoms and $R^{19}$ is H or $CH_3$.

11. Alkoxyamine initiators according to claim 10, wherein $R^8$=$R^9$=$R^{10}$=$R^{11}$=$CH_3$, $R^{17}$=H, OH, $NH_2$ or NHR and $R^{18}$=$CH_3$ or $C_4H_9$ and $R^{19}$=H or $CH_3$.

* * * * *